(12) United States Patent
Zwick et al.

(10) Patent No.: US 6,626,051 B2
(45) Date of Patent: Sep. 30, 2003

(54) LID FOR SAMPLE HOLDER

(75) Inventors: Michael Zwick, Vacaville, CA (US); Heather Koshinsky, El Cerrito, CA (US)

(73) Assignee: Investigen Biotechnologies, Inc., Hercules, CA (US)

( * ) Notice: Subject to any disclaimer, the term of this patent is extended or adjusted under 35 U.S.C. 154(b) by 0 days.

(21) Appl. No.: 09/930,099

(22) Filed: Aug. 14, 2001

(65) Prior Publication Data

US 2003/0033892 A1 Feb. 20, 2003

(51) Int. Cl.⁷ .................................................. B01L 3/00
(52) U.S. Cl. ................. 73/864.41; 73/863.31; 422/102; 422/103
(58) Field of Search ............... 73/864.91, 863.31; 422/102, 103; 141/236, 237; 220/86.1

(56) References Cited

U.S. PATENT DOCUMENTS

| | | | | |
|---|---|---|---|---|
| 4,857,274 A | * | 8/1989 | Simon ........................... | 422/72 |
| 5,182,082 A | * | 1/1993 | Monthony et al. ............. | 422/57 |
| 5,411,858 A | | 5/1995 | McGeehan et al. | |
| 5,447,079 A | * | 9/1995 | Neill et al. .................... | 73/863.23 |
| 5,817,510 A | * | 10/1998 | Pandey et al. ................. | 435/305.3 |
| 5,922,593 A | * | 7/1999 | Livingston .................... | 435/288.5 |
| 6,086,827 A | * | 7/2000 | Horner et al. ................. | 422/102 |
| 6,103,199 A | * | 8/2000 | Bjornson et al. .............. | 422/100 |
| 6,117,396 A | | 9/2000 | Demers | |
| 6,258,325 B1 | * | 7/2001 | Sanadi ........................... | 422/101 |
| 6,395,559 B1 | * | 5/2002 | Swenson ........................ | 436/180 |
| 6,485,690 B1 | * | 11/2002 | Pfost et al. .................... | 422/102 |
| 2001/0041357 A1 | * | 11/2001 | Fouillet et al. ................ | 435/91.1 |
| 2002/0039545 A1 | * | 4/2002 | Hall et al. | |
| 2002/0100714 A1 | * | 8/2002 | Staats ............................. | 210/85 |

FOREIGN PATENT DOCUMENTS

| | | |
|---|---|---|
| DE | 10046175 A1 | 3/2003 |
| WO | WO 97/33179 | 9/1997 |
| WO | WO 99/43432 | 9/1999 |
| WO | WO 00/13014 | 3/2000 |
| WO | WO 02/07423 A1 | 9/2002 |

\* cited by examiner

*Primary Examiner*—Helen Kwok
*Assistant Examiner*—C D Garber
(74) *Attorney, Agent, or Firm*—Morrison & Foerster LLP

(57) ABSTRACT

A lid for a sample holder that includes a load port, a first flow channel, and a second flow channel. The first flow channel includes a first end connected to the load port and a second end that opens into a first reservoir of the sample holder. The second flow channel also includes a first end connected to the load port and a second end that opens into a second reservoir of the sample holder.

64 Claims, 8 Drawing Sheets

LID FOR SAMPLE HOLDER

BACKGROUND

1. Field of the Invention

The present invention relates to sample holders. More particularly, the present invention relates to a lid for sample holders.

2. Description of the Related Art

Various tests, reactions, and assays in biology, chemistry, clinical diagnostics, and other areas are performed in sample holders having multiple reservoirs designed to retain various samples and/or solutions. One type of sample holder is a microtiter plate having multiple wells in which separate tests, reactions, and assays can be performed.

Microtiter plates have a number of wells arranged in various configurations. They typically come in standard sizes, such as 96 wells arranged in 8 rows and 12 columns, 12 wells arranged in 3 rows and 4 columns, and 384 wells arranged in 16 rows and 24 columns. However, microtiter plates can have any number of wells and the wells can be arranged in any configuration. Accordingly, the wells need not be arranged in columns and rows.

Some conventional covers for microtiter plates include a film that covers the entire microtiter plate. A disadvantage of these conventional covers is that a portion of the film must be removed from the microtiter plate in order to access and introduce materials into a single well, thereby exposing the well and surrounding wells to the environment and to each other. Exposing the wells in this manner can increase the potential for contamination of the contents of the wells and the surrounding environment.

Some conventional covers for microtiter plates include a lid that covers each well of the microtiter plate. A disadvantage of these conventional covers is that each lid must be removed separately to introduce material into multiple wells, which can be time and labor intensive. Additionally, when a lid is removed, contamination of the contents of the well and the surrounding environment can still occur.

SUMMARY

The present invention relates to a lid for a sample holder and a method of distributing fluid into the sample holder using the lid. In one embodiment of the present invention, a lid for a sample holder includes a load port and a first flow channel and a second flow channel. The first flow channel includes a first end connected to the load port and a second end that opens into a first reservoir of the sample holder. The second flow channel also includes a first end connected to the load port and a second end that opens into a second reservoir of the sample holder.

DESCRIPTION OF THE DRAWING FIGURES.

The present invention can be best understood by reference to the following description taken in conjunction with the accompanying drawing figures, in which like parts may be referred to by like numerals:

DETAILED DESCRIPTION

In order to provide a more thorough understanding of the present invention, the following description sets forth numerous specific details, such as specific configurations, parameters, and the like. It should be recognized, however, that such description is not intended as a limitation on the scope of the present invention, but is intended to provide a better description of exemplary embodiments.

Figure 3:
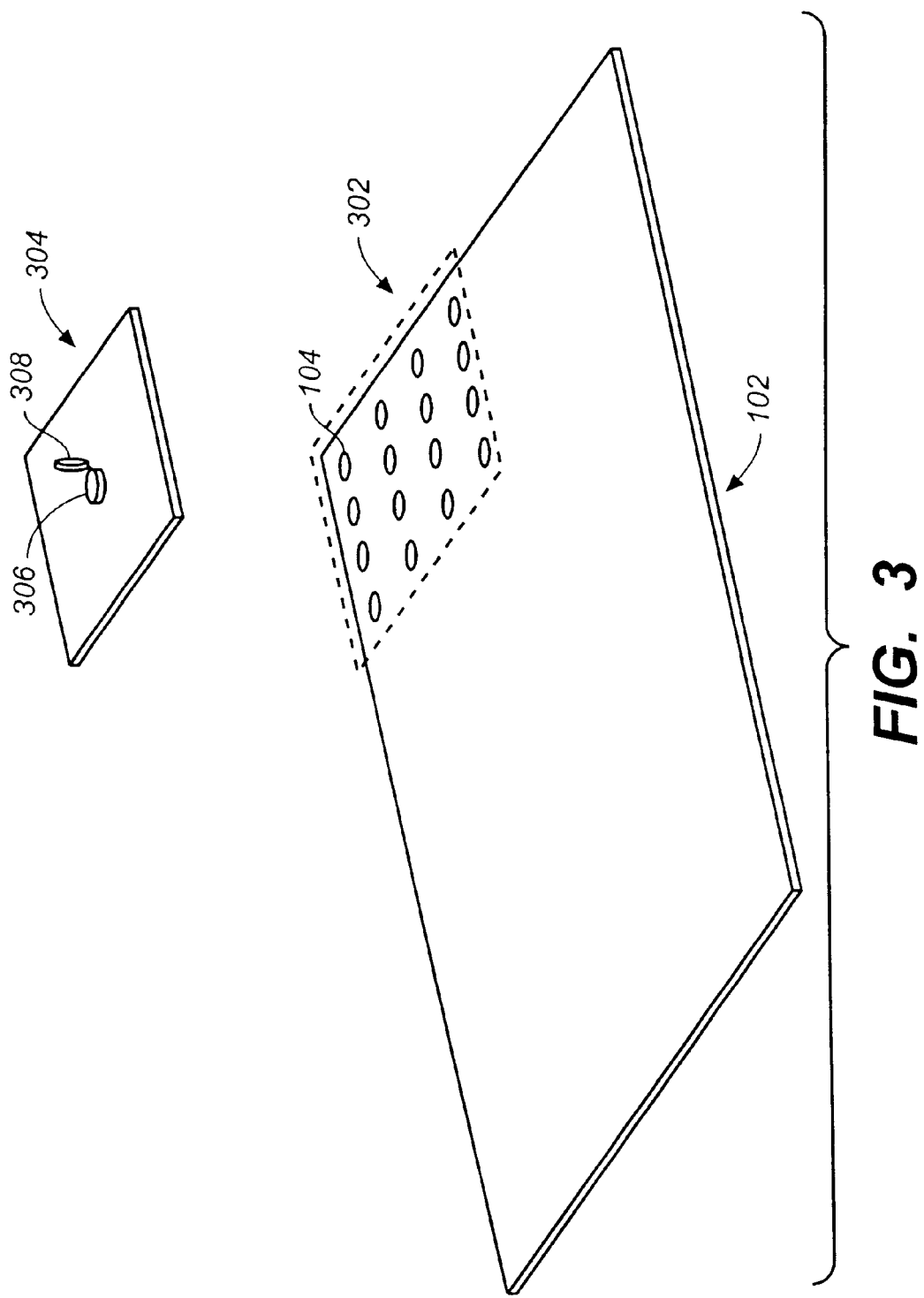
FIG. 3 is a perspective view of an exemplary embodiment.

With reference to FIG. 3, in accordance with one aspect of the present invention, a lid 304 can be configured to cover a section 302 of a microtiter plate 102 having a plurality of wells 104. Accordingly, lid 304 can reduce evaporation of the contents of wells 104. In addition, lid 304 can reduce the contamination of the contents of wells 104 from the surrounding environment and from other wells. In the exemplary embodiment depicted in FIG. 3, lid 104 is configured to cover a section 302 of a 96-well microtiter plate 102 having 16 wells arranged in 4 columns and 4 rows. It should be recognized, however, that lid 104 can be configured to cover any number of wells in any number of configurations. Furthermore, lid 104 can be configured to cover wells on any type of microtiter plate or sample holder.

Figure 5:
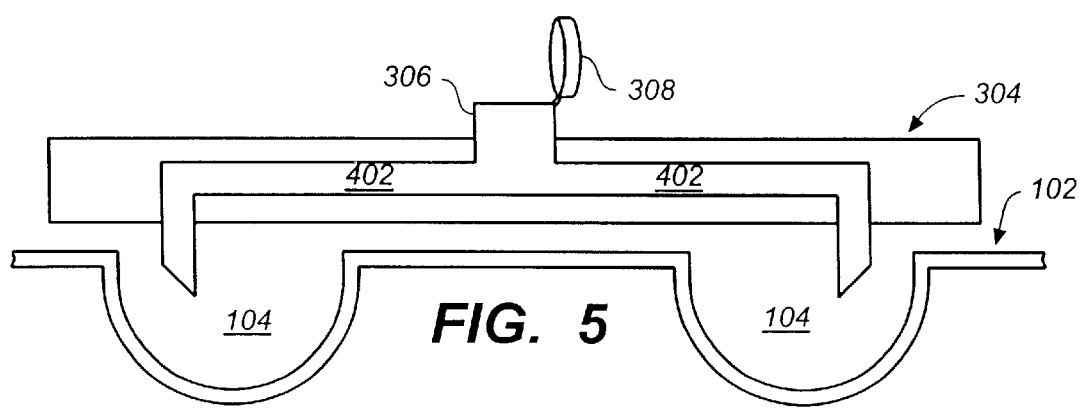
FIG. 5 is a cross-sectional view of another exemplary embodiment.

With reference to FIG. 5, in accordance with another aspect of the present invention, lid 304 can be configured to distribute fluid into wells 104. In the present embodiment, lid 304 includes a load port 306 configured to receive a fluid-dispensing device. More particularly, in one configuration, load port 306 includes a threaded locking mechanism, such as a lure lock, to receive a syringe. It should be recognized, however, that load port 306 can be configured to receive various dispensing devices, such as pipettes, pumps, automated dispensers, and the like. Additionally, although load port 306 is depicted as protruding from the surface of lid 304, it should be recognized that load port 306 can be flush with respect to the surface of lid 304. Alternatively, load port 306 can be recessed with respect to the surface of lid 304. In addition, it should be recognized that lid 304 can be configured with any number of load ports 306. Furthermore, each load port 306 can be configured to receive a different sample.

In the present embodiment, lid 304 also includes a plurality of flow channels 402. As depicted in FIG. 5, each flow channel 402 includes a first end connected to load port 306 and an open second end. When lid 304 is positioned over a section 302 of microtiter plate 102, the second end of flow channel 402 opens into well 104. In this manner, flow channels 404 can be configured to distribute fluid from load port 306 into wells 104.

As described above, in the present embodiment, lid 304 is configured to cover a section 302 of microtiter plate 102 having 16 wells 104 (FIG. 3). As such, with reference to FIG. 4, in the present embodiment, lid 304 includes 16 flow channels 402 to distribute fluid from load port 306 into 16 wells 104 through flow channels 402. However, as noted earlier, lid 304 can be configured to cover any number of wells 104. Similarly, lid 304 can be configured with any number of flow channels 402 to distribute fluid into any number of wells 104. For example, lid 304 can be configured to cover 4 wells and configured with 4 flow channels to distribute fluid to each of the 4 wells. However, lid 304 can also be configured to cover 4 wells and configured with 2 flow channels to distribute fluid to 2 of the 4 wells. In addition, lid 304 can be configured with any number of load ports 306, connected to any number of flow channels. For example, lid 306 can be configured to cover 6 wells and configured with 2 load ports, each of which is connected to 3 flow channels. However, lid 306 can also be configured to cover 6 wells and configured with 2 load ports, wherein one of the load ports is connected to 2flow channels and the other is connected to 3 flow channels.

In the present embodiment, the cross section of flow channels 402 is depicted as having a circular or an oval shape. One advantage of a circular or oval shaped cross section is that the amount of fluid lost within flow channel 402 as the fluid passes through flow channel 402 can be minimized. However, it should be recognized that the cross sections of flow channels 402 can have various shapes.

Additionally, the inner surface of flow channels 402 can be siliconized or treated in other ways to minimize the amount of sample lost within flow channels 402. It should be recognized, however, that for some applications, flow channels 402 may not need to be siliconized.

Furthermore, the cross sectional size of flow channels 402 can be adjusted to accommodate the amount of pressure that the fluid-dispensing device can provide to move the fluid through flow channels 402. More particularly, as noted earlier, various dispensing devices, such as pipettes, pumps, automated dispensers, and the like, can be used to introduce fluid into flow channels 402. These dispensing devices can provide different amounts of pressure to move the fluid through flow channels 402. For example, a pump can typically provide a greater amount of pressure than a pipette. As such, a relatively larger cross section can be used with a pump than a pipette. It should be recognized, however, that in some applications the fluid can flow through flow channels 402 under capillary action rather than or in addition to being actively pumped through flow channels 402.

With reference now to FIG. 5, flow channels 402 are depicted as having straight segments with square corners. One advantage of this configuration is that straight segments and square corners can be formed more easily than, for example, curved segments and rounded corners. It should be recognized, however, that flow channels 402 can include segments and corners having various shapes. For example, flow channels 402 can be formed with curved segments and rounded corners. One advantage of forming flow channels 402 with curved segments and rounded corners is that the amount of fluid lost within flow channel 402 as the fluid passes through flow channel 402 can be reduced. Additionally, as noted earlier, the cross sections of flow channels 402 can have various shapes.

Figure 4:
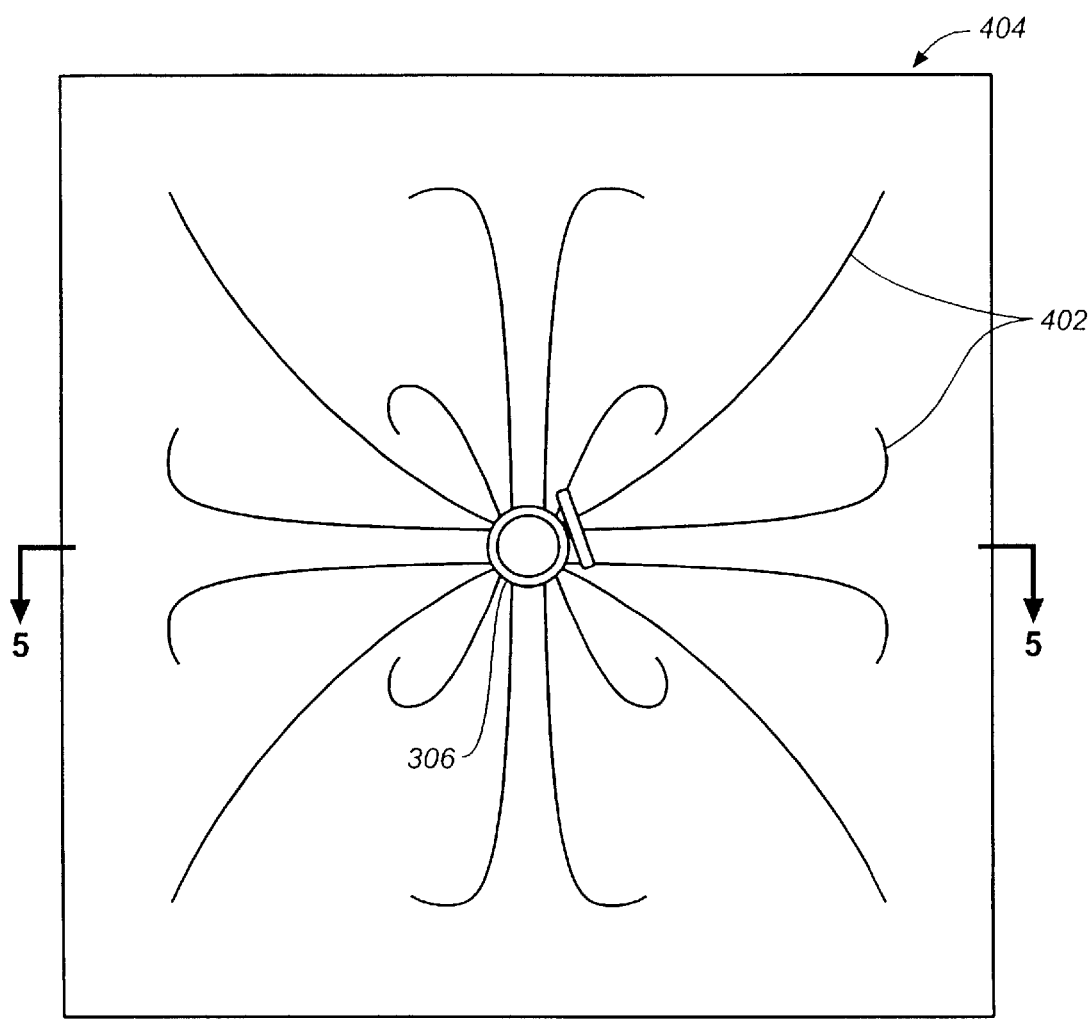
FIG. 4 is a top view of the embodiment in FIG. 3.

With reference to FIG. 4, flow channels 402 are depicted as extending out from load port 306 along a curvilinear path. One advantage of this configuration is that it can reduce turbulence and entrapment of air. However, it should be recognized that flow channels 402 can extend from load port 306 along paths of various shapes. For example, flow channels 402 can extend from load port 306 in straight segments with square corners.

Figure 6:
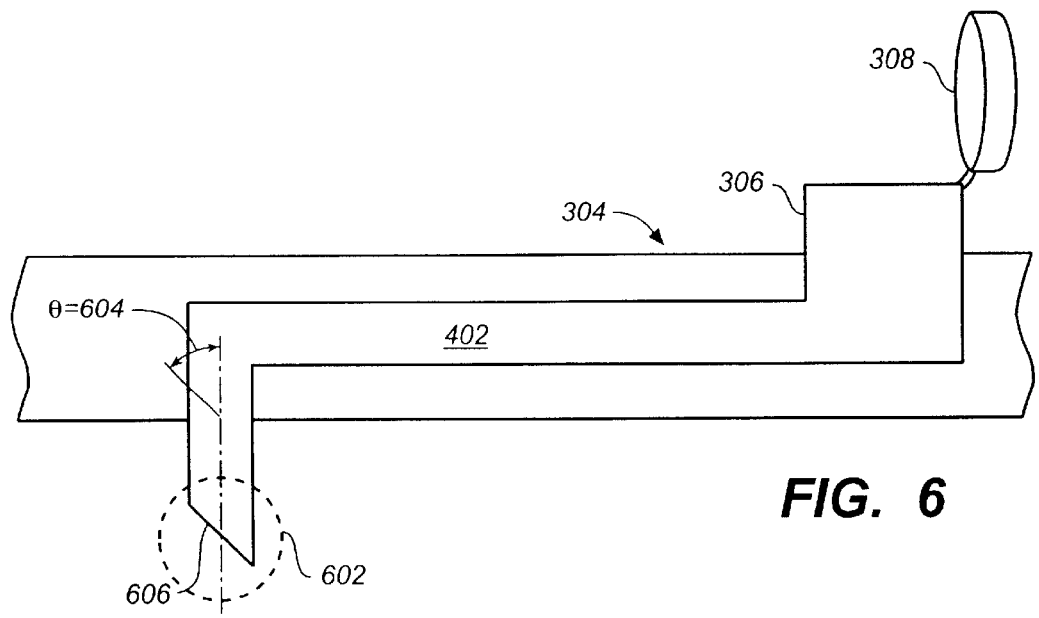
FIG. 6 is a cross-sectional view of a portion of the embodiment in FIG. 5.

With reference to FIG. 6, in the present embodiment, the second end of a flow channel 402 can include a beveled tip 602. As depicted in FIG. 6, beveled tip 602 is formed at an angle 604 with respect to the axis of flow channel 402. By adjusting angle 604, the surface area of surface 606 of beveled tip 602 can be adjusted. Accordingly, the size of the droplet formed by beveled tip 602 can be adjusted. As will be described below, increasing the size of the droplet can be advantageous in drawing fluid out of flow channel 402. However, it should be recognized that the second end of flow channel 402 can include a straight tip.

Figure 7:
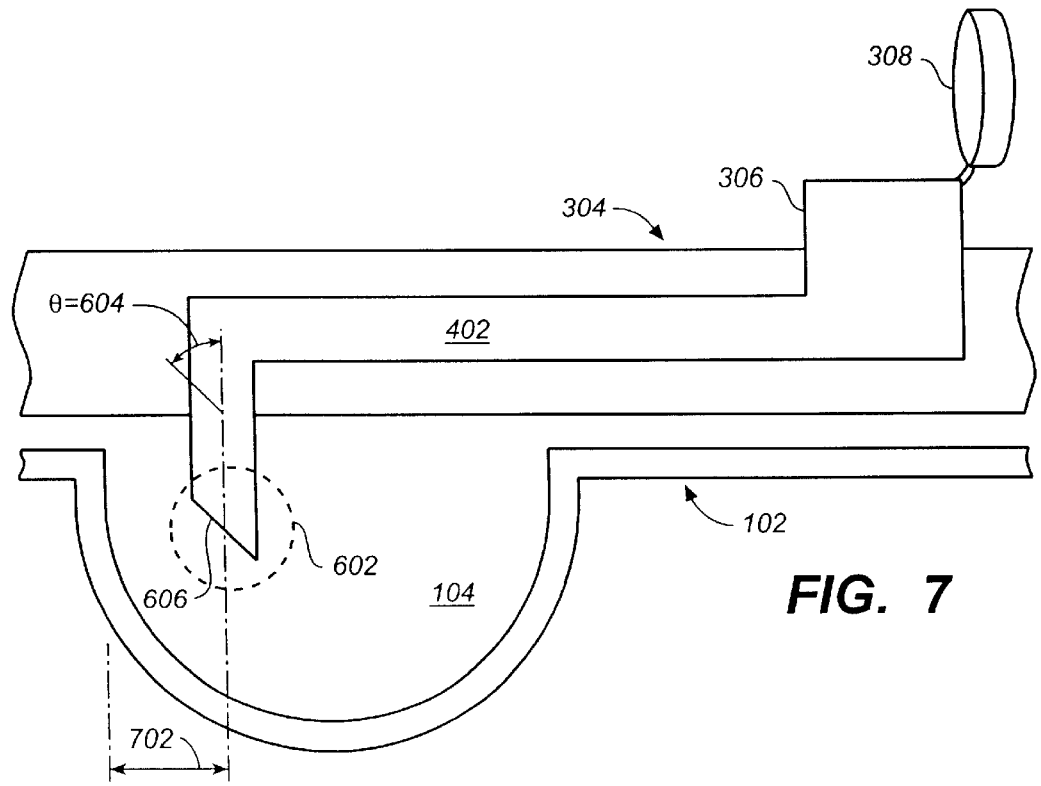
FIG. 7 is a cross-sectional view of another portion of the embodiment in FIG. 5.

With reference to FIG. 7, in the present embodiment, beveled tip 602 is positioned adjacent to the side of well 104 to provide a gap 702. Additionally, beveled tip 602 is positioned such that surface 606 faces the side of well 104. Gap 702 is selected such that a droplet emanating from beveled tip 602 can contact the side of well 104. In this manner, the droplet can be drawn out of beveled tip 602 assisted, in part, by surface tension. In a preferred embodiment, gap 702 is approximately 0.5 mm. It should be recognized, however, that gap 702 can vary. For example, as described above, the size of the droplet formed by beveled tip 602 can be adjusted by adjusting angle 604.

Additionally, in the present embodiment, well 104 can include glass fibers that facilitate drawing fluid into well 104 from beveled tip 602. Microtiter plate 102 and wells 104 can also be siliconized to facilitate the flow of droplets on the sides of well 104 to the bottom of well 104. However, it should be recognized that lid 304 can be used with a microtiter plate 102 having wells 104 that do not include glass fibers and are not siliconized.

With reference to FIG. 4, in accordance with another aspect of the present invention, lid 304 is configured to distribute approximately equal amounts of fluid to wells 104 (FIG. 5). In the present embodiment, load port 306 is positioned near the center of the lid 304 to distribute approximately equal amounts of fluid to each well 104 (FIG. 5) under lid 304. Additionally, in the present embodiment, flow channels 402 have approximately equal lengths and approximately equal cross sectional diameters to distribute approximately equal amounts of fluid to each well 104 (FIG. 5). In a preferred embodiment, approximately 20–50 $\mu$L are distributed to each well 104 (FIG. 5) within a tolerance of about 1 $\mu$L. It should be recognized, however, that the amount of fluid distributed to each well 104 (FIG. 5) and the acceptable tolerance can vary depending on the application.

Alternatively, it should be recognized that approximately equal amounts of fluid can be distributed to each well 104 (FIG. 5) through flow channels 402 of different lengths by correspondingly varying the cross sectional diameters of the flow channels 402. In particular, if a first flow channel 402 is greater in length than a second flow channel 402, then the first flow channel 402 should have a smaller cross sectional diameter than the second flow channel 402.

As described above and depicted in FIG. 4, in the present embodiment, load port 306 is positioned near the center of lid 304. It should be recognized, however, that load port 306 can be positioned in any location on lid 304. For example, load port 306 can be positioned toward one corner of lid 304. To distribute approximately equal amounts of fluid from load port 306, flow channels 402 can be either formed with approximately equal lengths and approximately equal cross sectional diameters, or formed with different lengths and correspondingly varying cross sectional diameters, as described above.

In addition to distributing approximately equal amounts of fluid from load port 306, lid 304 can be configured to distribute unequal amounts of fluid to wells 104 (FIG. 5). More particularly, if the flow channels 402 have approximately equal cross sectional diameters, the relative amount of fluid distributed to a particular well 104 (FIG. 5) can be controlled by varying the length of the flow channel 402 to that particular well 104 relative to the lengths of the other flow channels 402.

Additionally, it should be recognized that if the lengths of the flow channels 402 are approximately equal, the relative amount of fluid distributed to a particular well 104 (FIG. 5) can also be controlled by varying the cross sectional diameter of flow channel 402 to that particular well 104 (FIG. 5) relative to the cross sectional diameters of the other flow channels 402.

Alternatively, the relative amount of fluid distributed to a particular well 104 (FIG. 5) can be controlled by varying both the length and the cross sectional diameter of flow channel 402 to that particular well 104 (FIG. 5) relative to the lengths and cross sectional diameters of the other flow channels 402.

Figure 8:
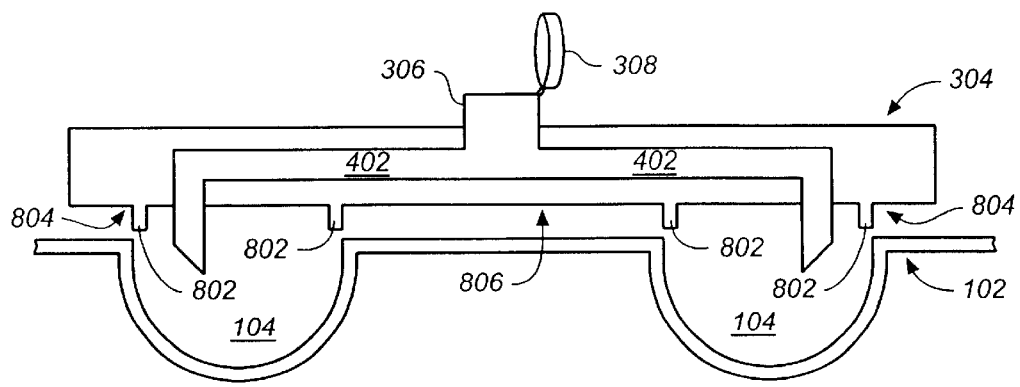
FIG. 8 is a cross-sectional view of still another exemplary embodiment.

With reference to FIG. 8, in another exemplary embodiment, lid 304 includes rings 802. As depicted in FIG. 8, ring 802 fits within well 104 to position lid 304. As described above, in the embodiment depicted in FIG. 7, beveled tip 602 is positioned adjacent the side of well 104 to provide gap 702. With reference again to FIG. 8, rings 802 can facilitate the proper positioning of lid 304 to provide for gap 702 (FIG. 7). It should be recognized that lid 304 need not include a ring 802 for every well 104 covered by lid 304 to position lid 304. For example, if lid 304 covers 16 wells arranged in 4 rows and 4 columns, lid 304 can include a ring 802 on two of the corners.

Additionally, it should be recognized that ring 802 need not be formed as a ring. For example, rings 802 can be formed as a plurality of tabs that extend into well 104. However, in some applications, rings 802 can be used to seal each well 104. In such applications, lid 304 can include a ring 802 for every well 104 to be sealed. Additionally, in such applications, rings 802 can be formed as an enclosed ring. It should be recognized, however, that the shape of rings 802 can depend on the shape of wells 104 and the particular application.

Figure 9:
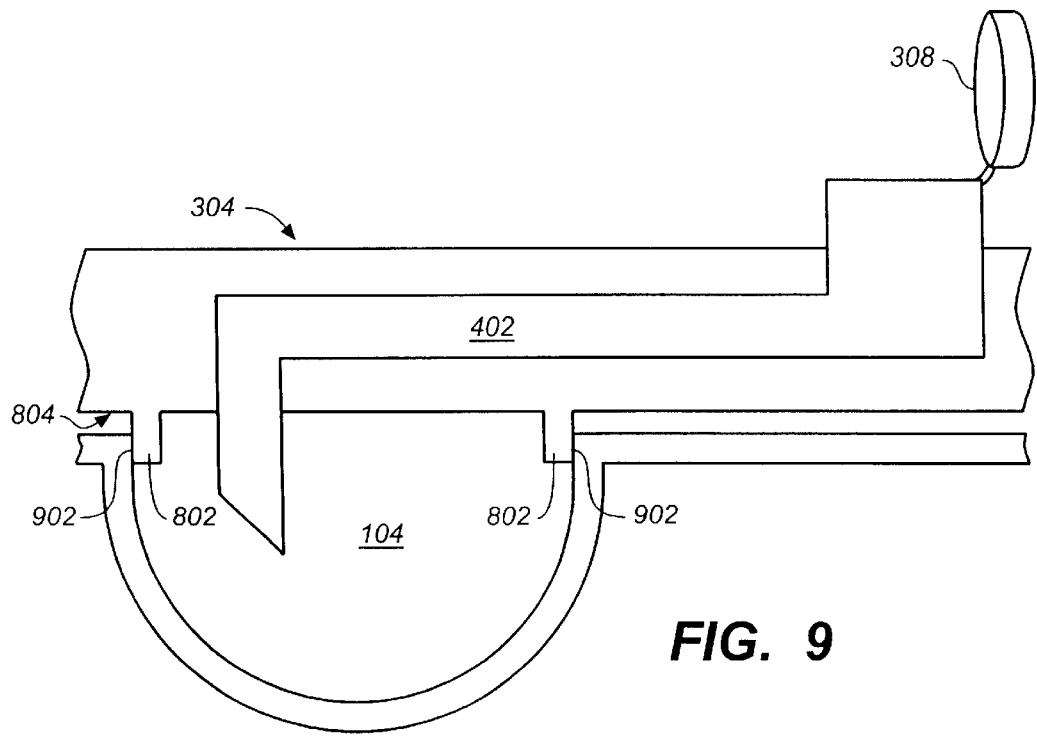
FIG. 9 is a cross-sectional view of the embodiment in FIG. 8.

As depicted in FIG. 9, in the present embodiment, ring 802 engages with the side of well 104 to secure lid 304 onto microtiter plate 102. It should be recognized, however, that lid 304 can be secured to microtiter plate 102 using other attachment mechanisms, such as teeth, latches, adhesives, and the like. Additionally, lid 304 and microtiter plate 102 can be fused together, such as by melting at least a portion of either one or both of the lid 304 and microtiter plate 102.

Figure 10:
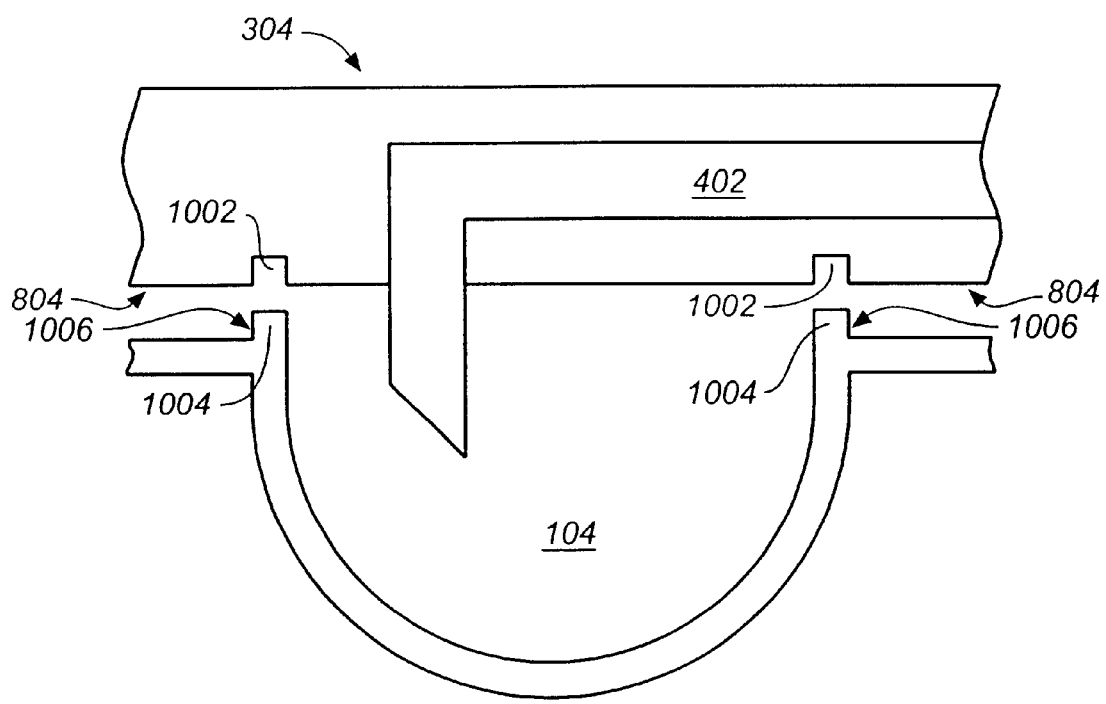
FIG. 10 is a cross sectional view of a portion of yet another exemplary embodiment.

Microtiter plate 102 can also be configured to engage with lid 304. For example, with reference to FIG. 10, microtiter plate 102 can include wells 104 with ridges 1004 and lid 304 can include matching channels 1002.

In some applications, lid 304 can be configured to form an air-type seal with microtiter plate 102. More particularly, in some applications, the section covered by lid 304 can be sealed with an air-tight seal, such as with an appropriate gasket, adhesive, and the like. In some applications, each individual well 104 can be sealed with an air-tight seal, such as with an appropriate gasket, adhesive, and the like.

Additionally, with reference to FIG. 5, load port 306 can include a cover 308. In some applications, cover 308 can also be configured to form an air-tight seal with load port 306. For example, a gasket can be used to form an air-tight seal between cover 308 and load port 306. However, it should be recognized that in some applications cover 308 can be omitted.

In accordance with another aspect of the present invention, lid 304 can be formed as two pieces joined together. Flow channels 402 can be formed by etching or molding portions of their cross-sectional profiles into the opposing surfaces that are joined together. Alternatively, one piece of lid 304 can be molded or etched with flow channels 402 then joined to a flat second piece. It should be recognized, however, that lid 304 and flow channels 402 can be formed using various methods. For example, lid 304 can be molded as a single piece with flow channels 402 formed within the mold. Alternatively, flow channels 402 can be formed or attached to the surfaces of lid 304.

Additionally, lid 304 can be constructed of various materials depending on the application. For example, lid 304 can be constructed of a biologically inert plastic that does not interfere with tests, reactions, assays, and the like in biology, chemistry, clinical diagnostics, and other areas in which the lid 304 may be used. Lid 304 can be formed from material that can withstand exposure to a range of temperatures without exhibiting any change in characteristics that would interfere with tests, reactions, assays, and the like in which lid 304 may be used. For instance, if lid 304 is used in conjunction with a polymerase chain reaction (PCR) assay, lid 304 can be constructed of materials that can withstand at least a range of temperatures between about 4° C. and about 98° C. See, e.g., James D. Watson et al., *Second Edition: Recombinant DNA* 82 (1992). However, it should be recognized that lid 304 can be constructed of materials that are not biologically inert or thermally resistant.

In some applications, lid 304 can be constructed of various materials having different thermal resistances, such that portions of lid 304 melt at a certain temperature, while other portions of lid 304 do not melt at this temperature. For example, with reference to FIG. 8, flow channel 402 depicted to the left of load port 306 can be constructed of a material that melts at a first temperature, while the rest of lid 304 is constructed of a material that melts at a second temperature, which is higher than the first temperature. When lid 304 is heated to the first temperature, flow channel 402 depicted to the left of load port 306 can melt shut, such that a sample cannot flow through it. At the same time, flow channel 402 depicted to the right of load port 306 is unaffected. In this manner, the number of active flow channels in lid 304 can be altered. It should be noted that lid 304 can be constructed of any number of different materials, such that heating lid 304 to different temperatures alters the number of active flow channels 402. For instance, lid 304 can be constructed of various materials, such that heating lid 304 to a first temperature inactivates two flow channels, further heating lid 304 to a second temperature greater than the first temperature inactivates two additional flow channels, and so forth.

In some applications, lid 304 can be constructed of materials that do not interfere with post amplification analysis of PCR products. For example, if lid 304 is used with a fluorescence detection system, lid 304 can be constructed of materials that have low levels of fluorescence and that do not autofluoresce if exposed to UV light, such as a polyethylene plastic that does not autofluoresce. In addition, lid 304 can be constructed of a material having sufficient optical clarity to allow lid 304 to be used with a fluorescence detection system without interfering with the analysis.

If lid 304 is used with an Enzyme-Linked Immunosorbent Assay (ELISA) plate reader, lid 304 can be constructed of materials that do not interfere with the efficiency of this detection system. For example, if the ELISA plate reader is used in conjunction with absorbance or colorimetric detection methods, lid 304 can be constructed of materials that minimize interference with the efficiency of these methods. Lid 304 can also be constructed of a material having sufficient optical clarity to allow lid 304 to be used with an ELISA plate reader without interfering with the analysis, such as polystyrene.

Figure 11:
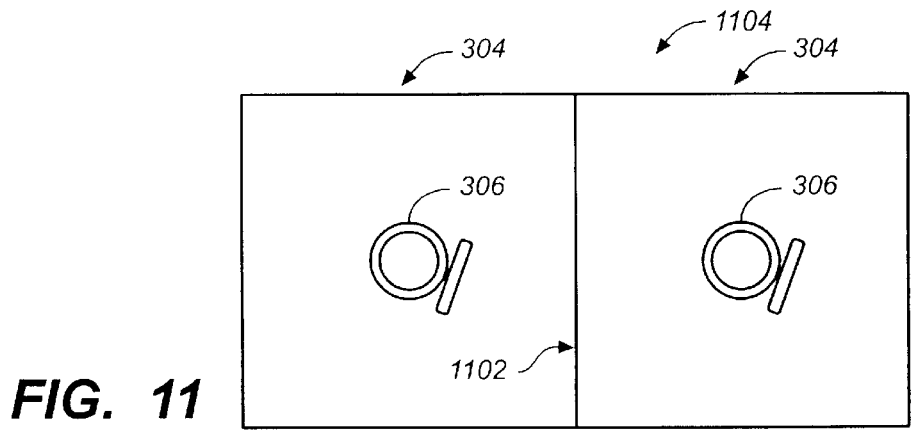
FIG. 11 is a top view of another exemplary embodiment.

With reference to FIG. 11, in accordance with another aspect of the present invention, multiple lids 304 can be combined to form multisection lid 1104 and utilized to cover multiple sections 302 of microtiter plate 102 (FIG. 3). Each of the two lids 304 includes a load port 306 configured to distribute fluid to wells 104 (FIG. 3) in a section 302 of the microtiter plate 102 (FIG. 3). As such, each load port 306 can be used to distribute a different fluid to the different sections 302 of microtiter plate 102 (FIG. 3). Multisection lid 1104 can be formed as a single unit, two lids 304 that are connected together at joints 1102 by any convenient method, or as two lids 304 that are adjacent but not connected.

Figure 12:
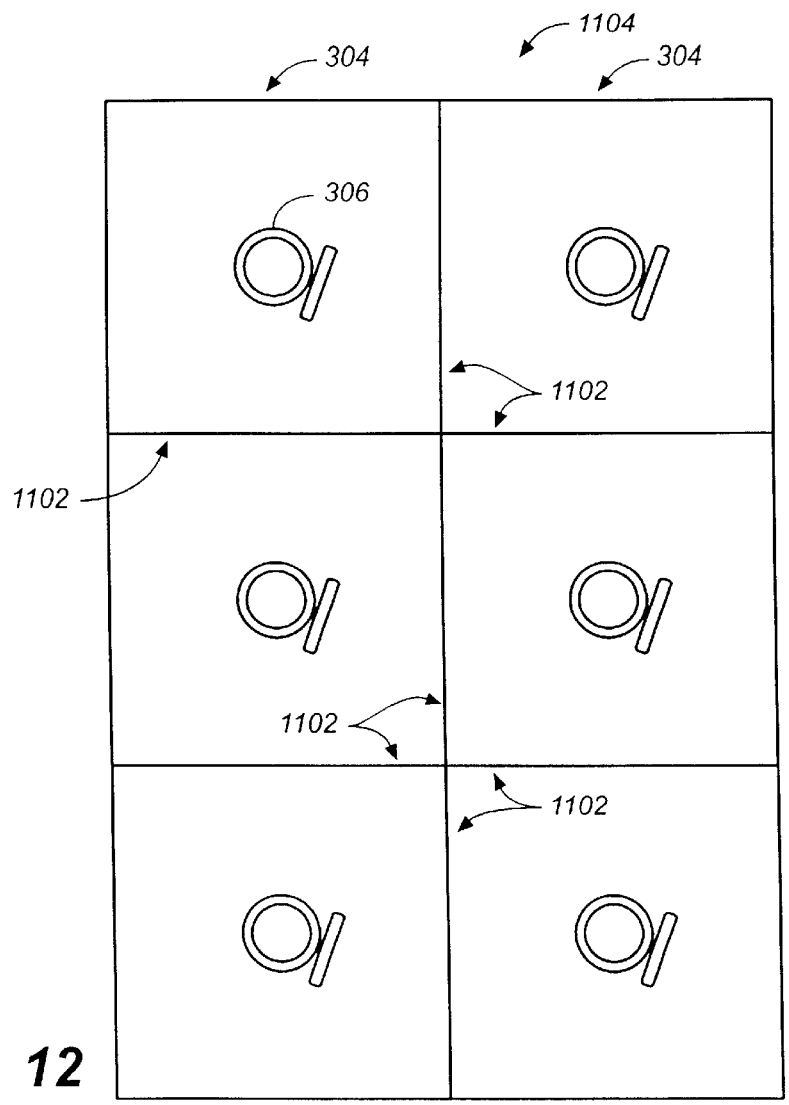
FIG. 12 is a top view of still another exemplary embodiment.

As described above, in the present embodiment, lid 304 can be configured to cover a section 302 of microtiter plate 102 (FIG. 3) having 16 wells arranged in 4 rows and 4 columns. Additionally, with reference to FIG. 1, in one exemplary application of the present invention, lid 304 can be used in connection with a microtiter plate 102 with 96 wells arranged in 8 rows and 12 columns. With reference to FIG. 12, 6 lids 304 can be arranged to partition microtiter plate 102 into 6 sections. In this manner, fluid can be introduced into the 96 wells of microtiter plate 102 through the 6 load ports 306 of lids 304. Additionally, different fluids can be introduced into each section of microtiter plate 102.

Figure 13:
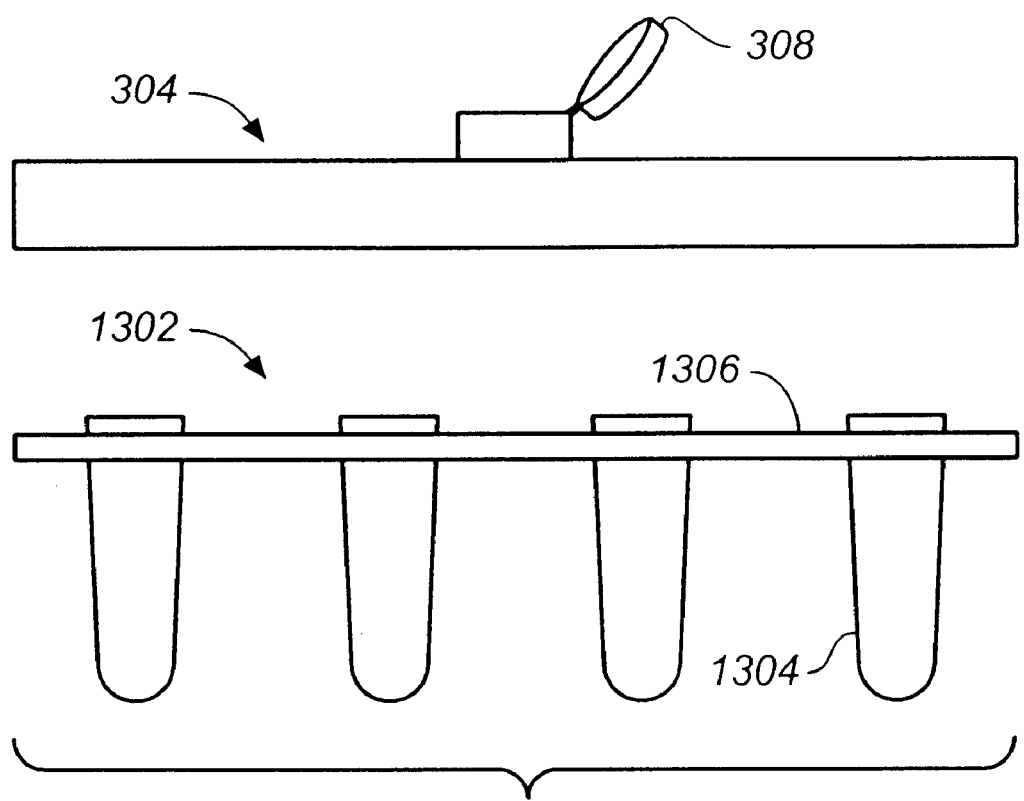
FIG. 13 is a side view of yet another exemplary embodiment.

As noted earlier, it should be recognized that microtiter plate 102 can include any number of wells arranged in various configurations. Additionally, lid 304 can cover any number of wells in various configurations. Furthermore, it should be recognized that lid 304 can be used with various types of sample holders. For example, with reference to FIG. 13, lid 304 can be used with sample holder 1302, which includes tray 1306 having vials 1304.

Having thus described various embodiments of lid 304, the following description will relate to the use of the lid 304 for PCR assays, which can be used to detect the presence of a particular DNA sequence in a sample. It should be recognized, however, that lid 304 can be used in performing various tests, reactions, assays, and the like in biology, chemistry, clinical diagnostics, and other areas.

In general, PCR can be used to amplify samples of DNA by repeatedly heating and cooling a mixture containing DNA, an oligonucleotide primer, an assortment of all four deoxyribonucleic precursors, DNA polymerase, and, when appropriate, a buffer. The mixture is first heated to temperatures sufficient to separate DNA strands. The mixture is then cooled to temperatures appropriate to allow primers to bind to the DNA strands. The mixture is then reheated to temperatures sufficient to allow the polymerase to synthesize new DNA strands by binding the precursors to appropriate locations on the separated DNA strands. The process can be repeated in order to double the concentration of the DNA sample in each cycle. Successful amplification of the DNA samples can be detected by fluorescence, absorbance, or calorimetric methods, using, for instance, a fluorescence detection system or ELISA plate reader, as appropriate.

In one exemplary application, lid 304 and microtiter plate 102 can be used to perform a PCR assay to test for hepatitis. As described above, with reference to FIG. 12, multiple lids 304 can be used to partition microtiter plate 102 (FIG. 1) into multiple sections 302 (FIG. 3). Each section 302 (FIG. 3) can be used to test a sample from a single patient. Accordingly, samples from different patients can be tested using a single microtiter plate 102.

Figure 1:
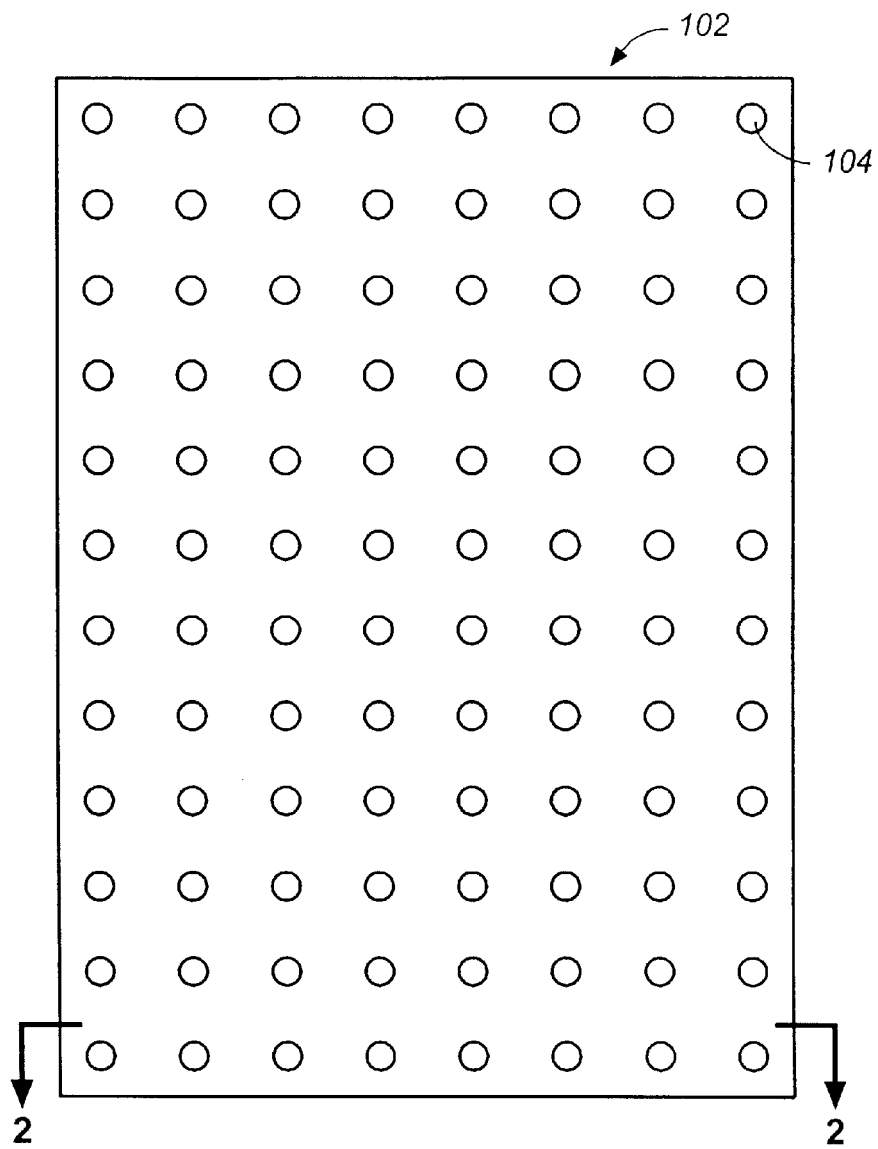
FIG. 1 is a top view of a microtiter plate.
Figure 2:
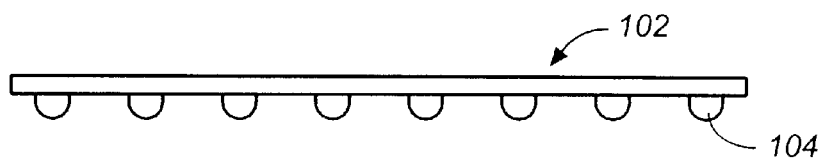
FIG. 2 is a cross-sectional view of the microtiter plate in FIG. 1.

With reference to FIG. 1, in one exemplary application, before using lids 304, each well 104 of a microtiter plate 102 can be pre-loaded with a diagnostic substance that contain the components for a PCR reaction, except a sample from a patient, such that each section 302 of the microtiter plate 102 has wells 104 containing diagnostic substances for testing hepatitis A, B, and/or C, including diagnostic substances that can be used as controls or negative controls. The diagnostic substances can be lyophilized and stuck to the bottom of each well where they are chemically stable and unable to move.

As depicted in FIG. 12, 6 lids 304 can then be used to partition the microtiter plate 102 (FIG. 1) into 6 sections 302 (FIG. 3) with 16 wells in each section 302. Plate 102 covered with lids 304 can now be used to test samples from patients.

A different sample of DNA is distributed to each section 302 of microtiter plate 102 (FIG. 3) through each load port 106. After microtiter plate 102 (FIG. 3) is exposed to the heating and cooling cycles of the PCR, the samples of DNA should be amplified in wells 104 (FIG. 3) of microtiter plate 102 (FIG. 3) that would yield a positive result. For instance, if the 6 samples correspond to 6 different people, then if all 6 people have hepatitis A, then the DNA in wells 104 (FIG. 3) containing the diagnostic substance for hepatitis A in each section 302 (FIG. 3) of the microtiter plate 102 (FIG. 3) should be amplified.

Accordingly, in this manner, a screen test for hepatitis A, B, and/or C can be performed on 6 different samples that correspond to 6 different people, within a single microtiter plate 102. Additionally, 16 tests can be conducted for a single person by loading a DNA sample from this person into a single load port 306 and thereby distributing the DNA sample to each of 16 wells 104 containing different diagnostic substances, respectively. In comparison, a manual process for loading each of the wells 104 with a sample would have been more labor intensive and time consuming, and an automated process for loading each well individually can be more costly.

Additionally, lids 304 can reduce contamination between wells in a section, between sections in microtiter plate 102, and between microtiter plate 102 and the surrounding environment. Lids 304 can also reduce evaporation and condensation of substances in wells 104 (FIG. 1). In addition, lids 304 can contain samples within the wells of microtiter plate 102 and minimize human exposure to the samples within the wells.

Although the present invention has been described with respect to certain embodiments, configurations, examples, and applications, it will be apparent to those skilled in the art that various modifications and changes may be made without departing from the invention.

We claim:

1. A lid for a sample holder, the sample holder having at least a first reservoir and a second reservoir, the lid comprising:

a load port;

a first flow channel having a first end connected to said load port and a second end that opens into the first reservoir when the lid covers the sample holder; and a second flow channel having a first end connected to said load port and a second end that opens into the second reservoir when the lid covers the sample holder, wherein said second end of said first flow channel ends in a beveled tip, wherein said beveled tip is positioned at a distance from a surface of the first reservoir when the lid covers the sample holder, and wherein said distance allows fluid from said beveled tip to contact the surface to draw the fluid from said beveled tip by surface tension.

2. The lid of claim 1, wherein said first flow channel and second flow channel are configured to allow distribution of equal amounts of fluid to said first reservoir and said second reservoir.

3. The lid of claim 2, wherein said first flow channel and said second flow channel have equal lengths.

4. The lid of claim 3, wherein said load port is disposed at the center of the lid.

5. The lid of claim 1, wherein said load port is configured to interface with a fluid-dispensing device.

6. The lid of claim 5, wherein said fluid-dispensing device is a syringe.

7. The lid of claim 6, wherein said load port includes a threaded locking mechanism.

8. The lid of claim 5, wherein said fluid-dispensing device is a pipette.

9. The lid of claim 1, wherein said first flow channel and said second flow channel are siliconized.

10. The lid of claim 1, wherein said first flow channel and said second flow channel are configured to allow fluid to pass from said first end to said second end of said first flow channel and said first end to said second end of said second flow channel by pressure.

11. The lid of claim 1, wherein said first flow channel and said second flow channel are configured to allow fluid to pass from said first end to said second end of said first flow channel and said first end to said second end of said second flow channel by capillary action.

12. The lid of claim 1, wherein said first flow channel and said second flow channel are configured to allow fluid to passively flow from said first end to said second end of said first flow channel and said first end to said second end of said second flow channel.

13. The lid of claim 1, wherein said first flow channel includes at least one curved segment.

14. The lid of claim 1, wherein said first flow channel includes at least one straight segment.

15. The lid of claim 1, wherein said distance is about 0.5 mm.

16. The lid of claim 1, wherein the lid is removably attached to a section of the sample holder by an attachment mechanism.

17. A The lid of claim 16, wherein said attachment mechanism forms an air-tight seal between the lid and said section.

18. The lid of claim 1, wherein the lid is fixed to a section of the sample holder by an attachment mechanism.

19. The lid of claim 18, wherein said attachment mechanism forms an air-tight seal between the lid and said section.

20. The lid of claim 1, wherein the lid is fused to the sample holder.

21. The lid of claim 1, wherein said load port includes a removable cover.

22. The lid of claim 21, wherein said cover forms an air-tight seal with said load port.

23. The lid of claim 1, wherein said first flow channel and second flow channel are configured to allow distribution of equal amounts of fluid to said first reservoir and said second reservoir.

24. A lid for a sample holder, the sample holder having at least a first reservoir and a second reservoir, the lid comprising:

a load part:

a first flow channel having a first end connected to said load port and a second end that opens into the first reservoir when the lid covers the sample holder;

a second flow channel having a first end connected to said load port and a second end that opens into the second reservoir when the lid covers the sample holder; and a ring disposed near said second end of said first flow channel, wherein said ring positions said second end of said first flow channel with respect to the first reservoir, wherein said ring allows the air-tight lid to enclose the first reservoir, and wherein said ring forms an air-tight seal between the lid and the first reservoir.

25. A lid for a sample holder, the sample holder having at least a first reservoir and a second reservoir, the lid comprising:

a load port;

a first flow channel having a first end connected to said load port and a second end that opens into the first reservoir when the lid covers the sample holder; and a second flow having a first end connected to said load port and a second end that opens into the second reservoir when the lid covers the sample holder, wherein said first flow channel is formed of a material having a different thermal resistance than said second flow channel.

26. The lid of claim 25, wherein said first flow channel and said second flow channel have equal lengths.

27. The lid of claim 26, wherein said load port is disposed at the center of the lid.

28. The lid of claim 25, wherein said load port is configured to interface with a fluid-dispensing device.

29. The lid of claim 28, wherein said fluid-dispensing device is a syringe.

30. The lid of claim 29, wherein said load port includes a threaded locking mechanism.

31. The lid of claim 29, wherein said distance is about 0.5 mm.

32. The lid of claim 28, wherein said fluid-dispensing device is a pipette.

33. The lid of claim 28, wherein said beveled tip is positioned at a distance from a surface of the first reservoir when the lid covers the sample holder, and wherein said distance allows fluid from said beveled tip to contact the surface to draw the fluid from said beveled tip by surface tension.

34. The lid of claim 25, wherein said first flow channel and said second flow channel are siliconized.

35. The lid of claim 25, wherein said first flow channel and said second flow channel are configured to allow fluid to pass from said first end to said second end of said first flow channel and said first end to said second end of said second flow channel by pressure.

36. The lid of claim 25, wherein said first flow channel and said second flow channel are configured to allow fluid to pass from said first end to said second end of said first flow channel and said first end to said second end of said second flow channel by capillary action.

37. The lid of claim 25, wherein said first flow channel and said second flow channel are configured to allow fluid to passively flow from said first end to said second end of said first flow channel and said first end to said second end of said second flow channel.

38. The lid of claim 25, wherein said first flow channel includes at least one curved segment.

39. The lid of claim 25, wherein said first flow channel includes at least one straight segment.

40. The lid of claim 25, wherein said second end of said first flow channel ends in a beveled tip.

41. The lid of claim 25, wherein the lid is removably attached to a section of the sample holder by an attachment mechanism.

42. The lid of claim 41, wherein said attachment mechanism forms an air-tight seal between the lid and said section.

43. The lid of claim 25, wherein the lid is fixed to a section of the sample bolder by an attachment mechanism.

44. The lid of claim 43, wherein said attachment mechanism forms an air-tight seal between the lid and said section.

45. The lid of claim 25, wherein the lid is fused to the sample holder.

46. A lid for a sample holder comprising:
a load port disposed on the lid;
a first flow channel formed within the lid,
said first flow channel having a first end connected to said load port and an open second end; and
a second flow channel formed within the lid,
said second flow channel having a first end connected to said load port and an open second end,
wherein said second end of said first flow channel ends in a beveled tip, and
wherein said beveled tip is positioned at a distance from a surface of the first reservoir when the lid covers the sample holder, and wherein said distance allows fluid from said beveled tip to contact the surface to draw the fluid from said beveled tip by surface tension.

47. The lid of claim 46, wherein said second ends of said first and said second flow channels open into a first and a second reservoir, respectively, of the sample holder.

48. The lid of claim 47, wherein said first and second flow channels are configured to distribute equal amounts of fluid to said first reservoir and said second reservoir.

49. The lid of claim 48, wherein said first flow channel and said second flow channel have equal lengths.

50. The lid of claim 49, wherein said load port is disposed at the center of the lid.

51. The lid of claim 46, wherein said load port is configured to interface with a fluid-dispensing device.

52. The lid of claim 46, wherein said first flow channel and said second flow channel are siliconized.

53. The lid of claim 46, wherein said first flow channel and said second flow channel are configured to allow fluid to pass from said first end to said second end of said first flow channel and said first end to said second end of said second flow channel by pressure.

54. The lid of claim 46, wherein said first flow channel and said second flow channel are configured to allow fluid to pass from said first end to said second end of said first flow channel and said first end to said second end of said second flow channel by capillary action.

55. The lid of claim 46, wherein said first flow channel and said second flow channel are configured to allow fluid to passively flow from said first end to said second end of said first flow channel and said first end to said second end of said second flow channel.

56. The lid of claim 46, wherein said first flow channel includes at least one curved segment.

57. The lid of claim 46, wherein said first flow channel includes at least one straight segment.

58. The lid of claim 46, wherein said distance is about 0.5 mm.

59. A method of distributing a fluid into at least a first reservoir and a second reservoir of a sample holder comprising:
positioning a fluid-dispensing device with respect to a load port formed on a lid, wherein said lid includes:
a first flow channel having a first end connected to said load port and an open second end, and
a second flow channel having a first end connected to said load port and an open second end; and
introducing the fluid into said load port with said fluid-dispensing device,
wherein the fluid flows from said load port into the first reservoir through said first flow channel, and from said load port into the second reservoir through said second flow channel, and
wherein said positioning further comprises engaging said fluid-dispensing device with a threaded locking mechanism in said load port.

60. The method of claim 59, wherein the fluid-dispensing device is a syringe.

61. The method of claim 59, wherein the fluid-dispensing device is a pipette.

62. The method of claim 59, wherein the amount of fluid flowing into said first and second reservoirs is equal.

63. The method of claim 59, wherein said first flow channel and said second flow channel have equal lengths.

64. The method of claim 59, wherein said load port is disposed at the center of the lid.

* * * * *